(12) United States Patent
Lin et al.

(10) Patent No.: US 10,932,699 B2
(45) Date of Patent: Mar. 2, 2021

(54) INVASIVE BIOSENSOR ALIGNMENT AND RETENTION

(71) Applicant: DexCom, Inc., San Diego, CA (US)

(72) Inventors: Arthur Lin, Fremont, CA (US); Xianyan Wang, San Jose, CA (US); Pey-Jiun Ko, Redwood City, CA (US)

(73) Assignee: DEXCOM, INC., San Diego, CA (US)

( * ) Notice: Subject to any disclaimer, the term of this patent is extended or adjusted under 35 U.S.C. 154(b) by 499 days.

(21) Appl. No.: 15/703,087

(22) Filed: Sep. 13, 2017

(65) Prior Publication Data
US 2019/0076069 A1    Mar. 14, 2019

(51) Int. Cl.
*A61B 5/145* (2006.01)
*A61B 5/00* (2006.01)
*A61B 5/0478* (2006.01)

(52) U.S. Cl.
CPC ........ *A61B 5/14503* (2013.01); *A61B 5/0478* (2013.01); *A61B 5/14532* (2013.01); *A61B 5/6833* (2013.01); *A61B 5/6848* (2013.01); *A61B 5/6898* (2013.01); *A61B 2560/0406* (2013.01); *A61B 2560/0431* (2013.01); *A61B 2560/0462* (2013.01); *A61B 2560/063* (2013.01); *A61B 2562/164* (2013.01)

(58) Field of Classification Search
CPC .............. A61B 5/14503; A61B 5/0478; A61B 5/14532; A61B 5/6848; A61B 5/6898; A61B 5/6833
See application file for complete search history.

(56) References Cited

U.S. PATENT DOCUMENTS

| | | |
|---|---|---|
| 5,167,641 A | 12/1992 | Schmitz et al. |
| 6,786,875 B2 | 9/2004 | Botich et al. |
| 7,169,600 B2 | 1/2007 | Hoss et al. |
| 8,457,708 B2 | 6/2013 | Brister et al. |
| 10,335,066 B2 * | 7/2019 | Peterson .............. A61B 5/6848 |

FOREIGN PATENT DOCUMENTS

| | | |
|---|---|---|
| EP | 1502614 A2 | 2/2005 |
| WO | WO 2014/072823 | 5/2014 |

OTHER PUBLICATIONS

Myheatsinks , "Heat Sink Attachment Screws and Hardware", [[http://www.myheatsinks.com/products/heat-sink-attachment/]] downloaded Sep. 13, 2017.
International Search Report and Written Opinion dated Oct. 18, 2018 for Application No. PCT/US2018/044710.

* cited by examiner

*Primary Examiner* — Eric J Messersmith
(74) *Attorney, Agent, or Firm* — Knobbe Martens Olson & Bear LLP

(57) ABSTRACT

Examples of invasive biosensor alignment and retention features and methods are described. One example biosensor includes a housing comprising: a first surface defining a first opening, and a second surface opposite the first surface, the second surface defining a second opening, the first and second openings defining a substantially unobstructed pathway through the housing; a biosensor wire partially disposed within the housing and having an exterior portion extending through the first opening; a hollow insertion needle positioned within the pathway and extending through the first opening, the hollow insertion needle at least partially encircling the biosensor wire; and a biosensor retention feature collapsible against the first surface of the housing, the biosensor retention feature encircling and contacting the hollow insertion needle.

15 Claims, 17 Drawing Sheets

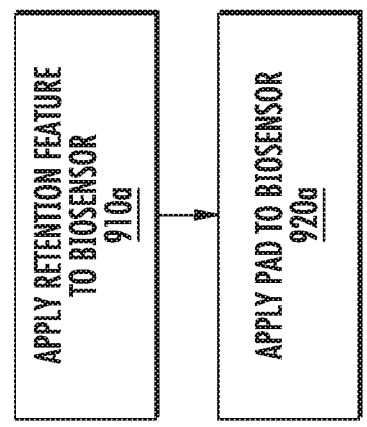
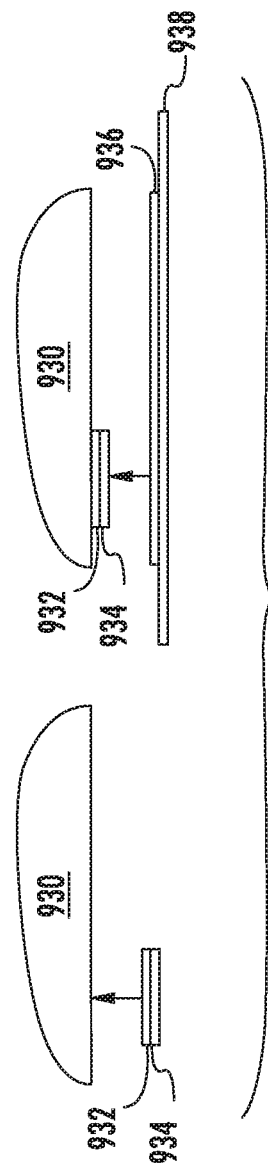

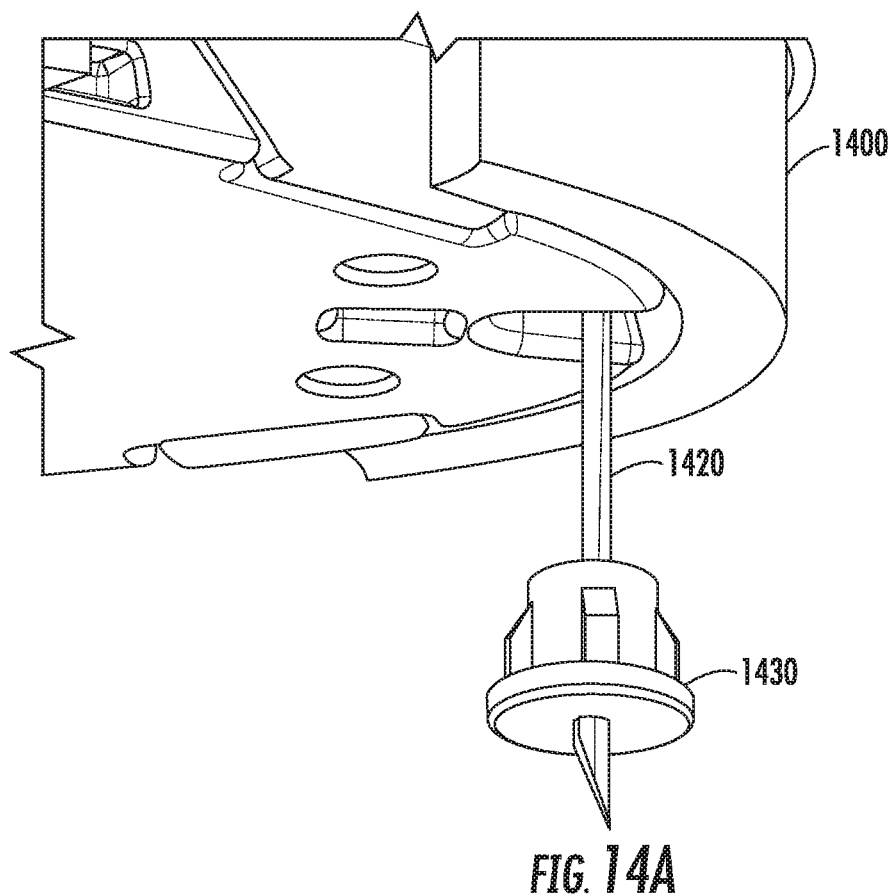
FIG. 14A
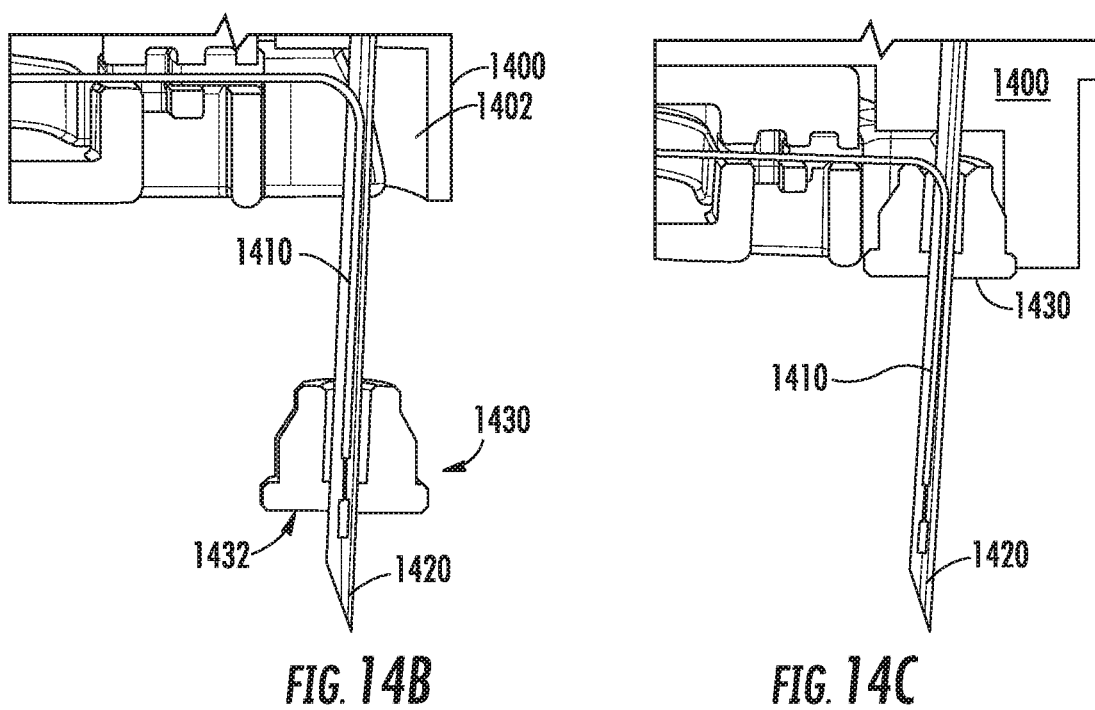
FIG. 14B
FIG. 14C

INVASIVE BIOSENSOR ALIGNMENT AND RETENTION

FIELD

The present application generally relates to invasive biosensors and more generally relates to invasive biosensor alignment and retention.

BACKGROUND

Wearable invasive biosensors, such as continuous glucose monitors ("CGMs"), employ sensor wires that are inserted into a wearer's skin to measure analytes, such as glucose levels. Because sensor wires typically have a small diameter and may not be able to puncture a wearer's skin without bending or breaking, a needle is used to create a puncture wound through which the sensor wire is inserted. In some cases, the needle is inserted through an opening in the biosensor and axially aligned with the sensor wire so that, when the CGM is pressed against the wearer's skin, the needle creates the puncture wound and the sensor wire is inserted through the puncture. The needle is then withdrawn, leaving the sensor wire in place.

SUMMARY

Various examples are described for invasive biosensor alignment and retention. One example wearable biosensor includes a housing comprising: a first surface defining a first opening, and a second surface opposite the first surface, the second surface defining a second opening, the first and second openings defining a substantially unobstructed pathway through the housing; a biosensor wire partially disposed within the housing and having an exterior portion extending through the first opening; a hollow insertion needle positioned within the pathway and extending through the first opening, the hollow insertion needle at least partially encircling the biosensor wire; and a biosensor retention feature collapsible against the first surface of the housing, the biosensor retention feature encircling and contacting the hollow insertion needle.

One example method for providing invasive biosensor alignment and retention includes providing a housing comprising: a first surface defining a first opening, and a second surface opposite the first surface, the first surface defining a second opening, the first and second openings defining a substantially unobstructed pathway through the housing; positioning a biosensor wire within the housing and a first portion of the biosensor wire extending through the first opening; inserting a hollow insertion needle into the pathway through the unobstructed pathway from the second opening and through the first opening, the hollow insertion needle at least partially encircling the first portion of the biosensor wire; applying a biosensor retention feature to the hollow insertion needle, the biosensor retention feature encircling and contacting the hollow insertion needle and configured to collapse against the bottom surface of the housing.

Another example wearable biosensor includes a housing comprising: a first surface defining a first opening, and a second surface opposite the first surface, the second surface defining a second opening, the first and second openings defining a substantially unobstructed pathway through the housing; a biosensor wire partially disposed within the housing and having an exterior portion extending through the first opening; a hollow insertion needle positioned within the pathway and extending through the first opening coaxially aligned with the exterior portion of the biosensor, the hollow insertion needle at least partially encircling the exterior portion of the biosensor wire; and means for maintaining coaxial alignment between the hollow insertion needle and the biosensor wire coupled to a portion of the hollow insertion needle coaxially aligned with the exterior portion of the biosensor wire.

An example method for applying a wearable biosensor includes obtaining a wearable biosensor comprising: a housing comprising a first surface defining a first opening, and a second surface opposite the first surface, the second surface defining a second opening, the first and second openings defining a substantially unobstructed pathway through the housing; a biosensor wire partially disposed within the housing and having an exterior portion extending through the first opening; a hollow insertion needle positioned within the pathway and extending through the first opening, the hollow insertion needle at least partially encircling the biosensor wire; and a biosensor retention feature collapsible against the first surface of the housing, the biosensor retention feature encircling and contacting the hollow insertion needle; applying the wearable biosensor to a wearer's skin comprising: inserting the hollow insertion needle into the wearer's skin through a puncture, inserting the biosensor wire through the puncture, and pressing the housing against the wearer's skin and collapsing the biosensor retention feature against the housing; and withdrawing the hollow insertion needle from the wearer's skin and the housing.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 9A-9B show an example method for assembling a biosensor alignment and retention feature;

FIGS. 14A-14C show an example biosensor alignment and retention feature;

DETAILED DESCRIPTION

Examples are described herein in the context of invasive biosensor alignment and retention. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

An invasive biosensor includes one or more sensing components that are inserted into a person's body, such as through the person's skin, and may measure analytes to determine information, such as glucose levels. For example, a continuous glucose monitor ("CGM") may be applied to and worn by a person (the "wearer") for a period of time to monitor the wearer's glucose levels. This example CGM includes a sensor wire that is inserted into the wearer's skin to access interstitial fluid and sense glucose levels. However, because the sensor wire is fragile at the intended thickness/diameter, 100 micrometers (or "microns") in this example, a needle is used to puncture the skin and insert the sensor wire. The example CGM is coupled to an insertion device with a hollow insertion needle, which is positioned coaxially with the CGM sensor wire, which is positioned within the hollow portion of the insertion needle. When the wearer applies the CGM, she will puncture her skin using the insertion needle and the sensor wire will follow the needle into the puncture. After the CGM sensor wire has been inserted into the puncture and the CGM is attached to the wearer's skin the wearer retracts the needle, leaving the sensor wire under the skin and the CGM in place.

Figure 1A:
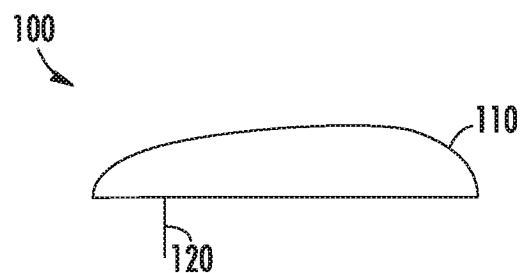
FIGS. 1A-1E show an example invasive biosensor and insertion needle and retention feature.
Figure 1B:
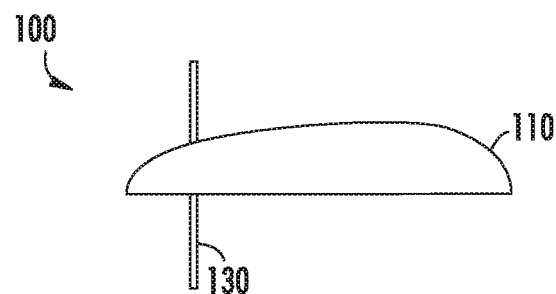

Referring to FIGS. 1A-1D, these figures show different views of the example CGM 100, which has a housing 110 and a sensor wire 120. As can be seen in FIG. 1A, the sensor wire 120 extends out of the housing 110 so that it may be inserted into the wearer's skin and the housing can 110 be affixed to the wearer's skin To apply the CGM 100, and as shown in FIG. 1B, a needle 130 (also referred to as an "insertion needle") is inserted through a hole in the upper surface of the CGM 100, through a cavity formed within the interior of the CGM 100 to accommodate the needle 130 and the sensor wire 120, and through a hole in the lower surface of the CGM 100. The needle 130 is inserted so that it aligns axially with the sensor wire 120. Thus, the CGM 100, the needle 130, and the sensor wire 120 can all be pressed against the wearer's skin to apply the CGM 100 in a single motion. As the CGM 100 is pressed against the wearer's skin, the needle 130 punctures the skin and the sensor wire 120 is pressed through the puncture. The CGM 100 is then pressed against the wearer's skin, where it remains, e.g., via pressure-sensitive adhesive ("PSA"). The needle 130 is then withdrawn, leaving the CGM 100 and sensor wire 120 in place.

Figure 1C:
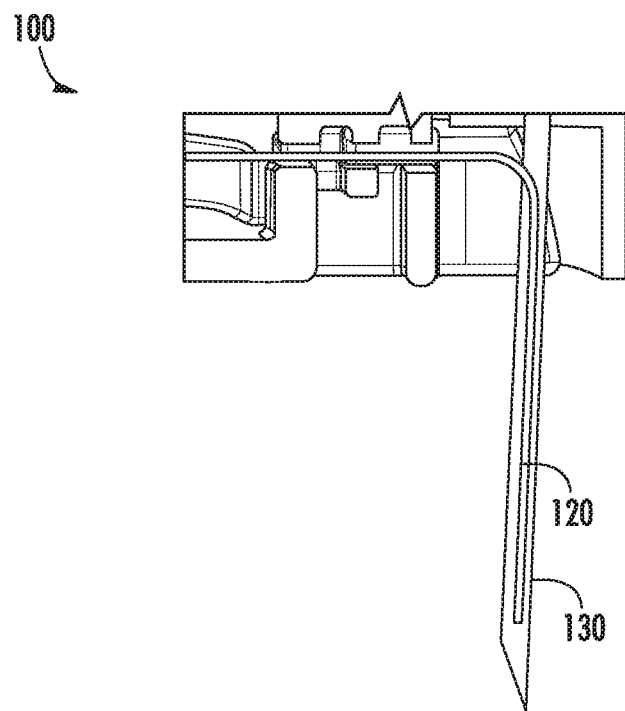
Figure 1D:
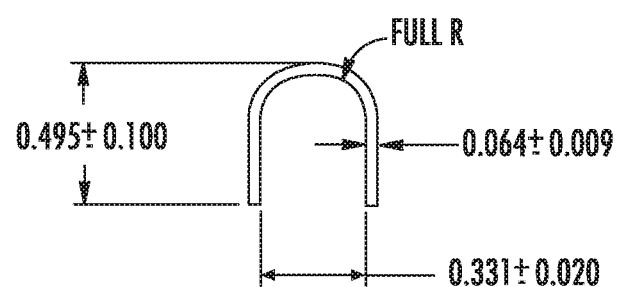

FIGS. 1C-1D illustrate how the needle 130 and the sensor wire 120 engage to allow substantially simultaneous insertion into the wearer's skin. The insertion needle 130 in this example is hollow and has an open cross-section as illustrated in FIG. 1D, which may be referred to as having a "C" or "U" shape, and extends slightly beyond the end of the sensor wire 120. The amount by which the needle extends beyond the sensor wire is not material; though puncturing the wearer's skin to a depth beyond what is needed to insert the sensor wire 120 should be avoided as causing unnecessary pain or trauma to the wearer. As can be seen in FIG. 1D, the needle's cross section has a larger diameter than the sensor wire 120. By orienting and positioning the needle 130 to enclose the sensor wire 120 within its hollow cross-section, the needle 130 and sensor wire 120 can be positioned co-axially and thus, when the wearer presses needle 130 into the wearer's skin to create a puncture, the sensor wire 120 can immediately travel into the puncture created by the needle 130.

However, in some examples, the CGM 100 may be packaged with the insertion needle 130 already coupled to the CGM 100. Thus, the user may obtain a new CGM 100 and not be required to insert the needle through the CGM 100 to them apply the CGM 100. However, because the packaged CGM 100 may be subjected to various forces during manufacturing, packaging, and transportation, the sensor wire 120 and needle 130 may become unaligned. For example, the sensor wire 120 may be jolted or bent out of the C-shaped cross-section, such as following the package being dropped. To help maintain the co-axial arrangement of the needle 130 and sensor wire 120 while subcutaneously inserting the sensor wire 120, the CGM 100 has a sensor alignment and retention feature coupled to its bottom surface.

Figure 1E:
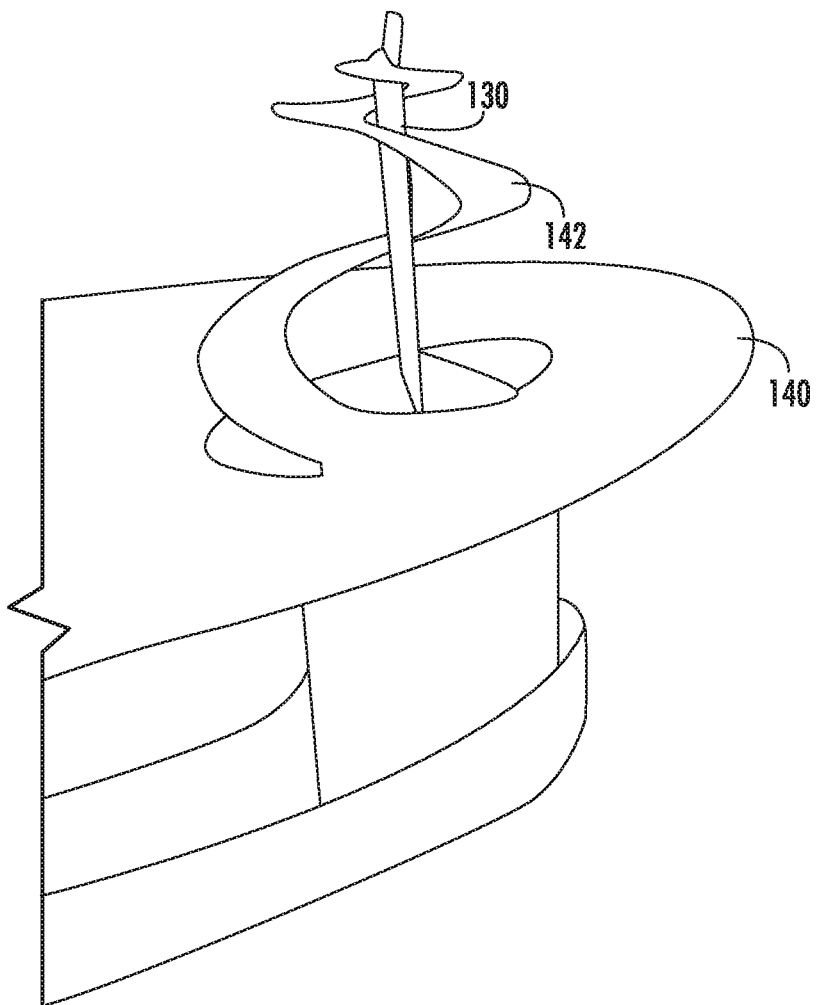

Referring now to FIG. 1E, FIG. 1E illustrates the bottom surface of the CGM 100 with an attached sensor alignment and retention feature 140 (or "retention feature"). The retention feature 140, in this example, includes a portion adhered to the bottom surface of the CGM 100, such as by a PSA. In addition, the retention feature has an extendible portion 142 that has been cut and spirals upwards around the insertion needle 130. During manufacturing, the extendible portion 142 has been pulled away from the bottom surface of the CGM 100 to form a spiral shape. The tip of the cut portion 142 contains a close fitting hole which fits around and engages with the needle 130, thereby helping to prevent the sensor wire 120 from dislodging from within the cross-section of the hollow insertion needle 130. When the CGM 100 is later applied to a wearer's skin, the extendible portion 142 collapses and flattens back against bottom surface of the CGM 100 as it is pressed against the wearer's skin, before ultimately lying flush against the bottom surface of the CGM 100. Thus, the extendible portion 142 helps maintain co-axial alignment between the sensor wire 120 and insertion needle 130, while not affecting the CGM's insertion procedure.

This illustrative example is given to introduce the reader to the general subject matter discussed herein and the disclosure is not limited to this example. The following sections describe various additional non-limiting examples and examples of systems and methods for invasive biosensor alignment and retention. FIGS. 2A-14B illustrate further examples of means for maintaining coaxial alignment between a hollow insertion needle and a biosensor wire and are described in more detail below.

Figure 2A:
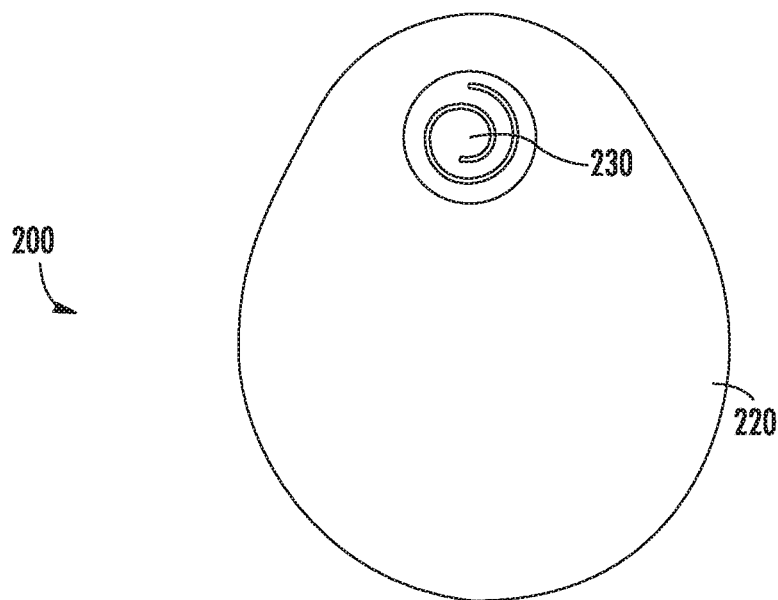
FIGS. 2A-2B show an example biosensor alignment and retention feature according to this disclosure.
Figure 2B:
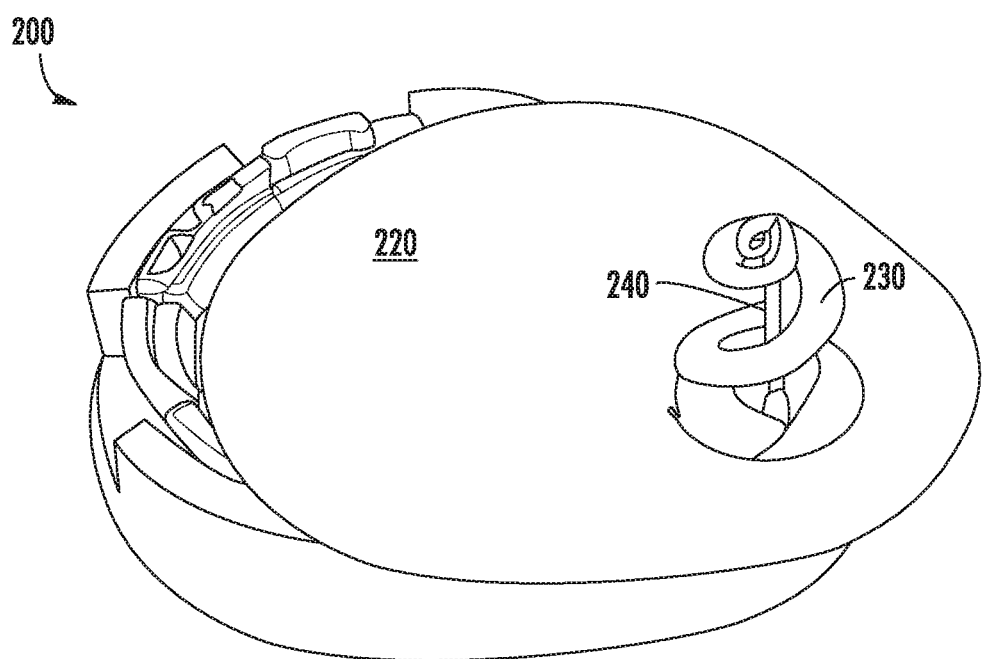

Referring now to FIGS. 2A-2B, FIGS. 2A-2B show an example sensor alignment and retention feature 210 according to this disclosure. The retention feature 210 in this example includes a pad (or backing material) 220 that may be used to couple the retention feature 210 to a biosensor, such as a CGM. The pad 220 may be shaped during the manufacturing process to correspond to the shape of a lower surface of a biosensor, or to a portion of such a shape. The retention feature 210 also includes an extendable portion 230 that may be extended during manufacturing, or when an insertion needle is inserted through the CGM, to form a spiral shaped feature to retain a co-axial alignment between a sensor wire and insertion needle. In FIG. 2A, the extendable portion has not yet been extended and thus remains flush with the pad 220. This helps illustrate the shape of the cut used to form the cut portion 230 and enable extension of the cut portion to create the spiral shape.

In this example and during the manufacturing process, the pad 220 is formed of a polyurethane foam, but may be constructed of other materials, such as cloth, silicone, etc. The extendable portion 230 in this example is formed from a different piece of material than the pad 220 and is coupled to the pad by an adhesive. However, in some examples, the extendable portion 230 may be formed from the same piece of material as the pad 220. In some examples, as will be discussed in more detail below with respect to FIGS. 6-10, a pad may be formed from multiple layers coupled to each other. The extendable portion 230 may be formed from any suitable material, including polyurethane foam, silicone, etc. Further, in some examples, the retention feature may not include the pad 220, but may instead only include the cut portion 230.

FIG. 2B illustrates the retention feature 210 affixed to a lower surface of an invasive biosensor 200. As can be seen, the pad 220 generally corresponds to the shape of the bottom surface of the biosensor 200, though it does not cover the entire bottom portion in this example. It should be appreciated that the pad 220 can be any suitable size and shape, depending on the application. For example, during the manufacturing process, the pad 220 may be shaped and sized to match the shape and size of the bottom surface of the biosensor 200. In some examples the pad 220 may extend beyond one or more edges of the bottom surface of the biosensor 200, or may only cover a portion of the bottom surface of the biosensor 200.

Figure 3:
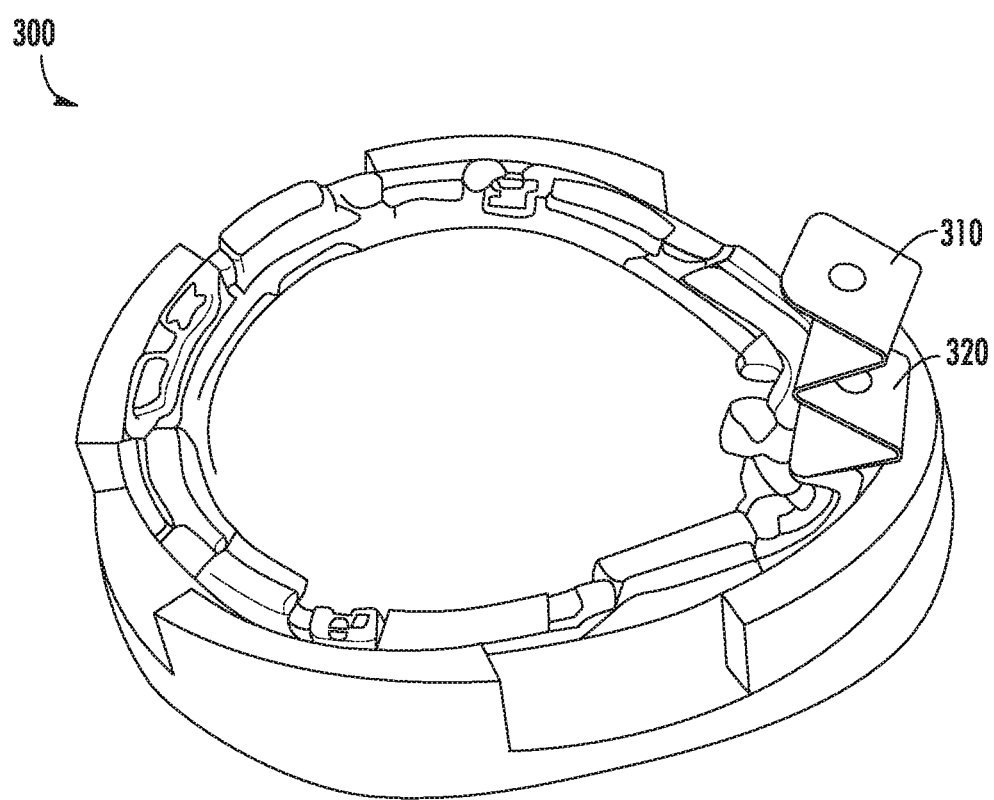
FIG. 3 shows an example biosensor alignment and retention feature according to this disclosure.

Referring now to FIG. 3, FIG. 3 shows an example sensor alignment and retention feature 310 (or just "retention feature") according to this disclosure. In this example, the retention feature 310 comprises an "accordion" shape. During the manufacturing process, a length of material has been folded back on itself multiple times and a hole having a diameter a few tens of microns wider than the needle has been cut through the material to engage with and encircle the insertion needle 320. By engaging and encircling the insertion needle 320 in this example, a sensor wire positioned within the hollow portion of the needle may be retained. In the event of a shock or force applied to the sensor wire, it may be retained in place within the hollow portion of the needle by the retention feature. Further, when the biosensor 300 is applied to the wearer, the retention feature 310 may fold and collapse against the bottom surface of the biosensor 300.

While the example shown in FIG. 3 does not include a pad, such as discussed above with respect to FIGS. 2A-2B, in some examples, the retention feature may also include or be coupled to a pad. As discussed above with respect to the examples of FIGS. 2A-2B, any suitable pad may be employed. Further, the retention feature 310 may be separately constructed and then coupled to a pad, or may be formed from the same piece of material as the pad.

Figure 4A:
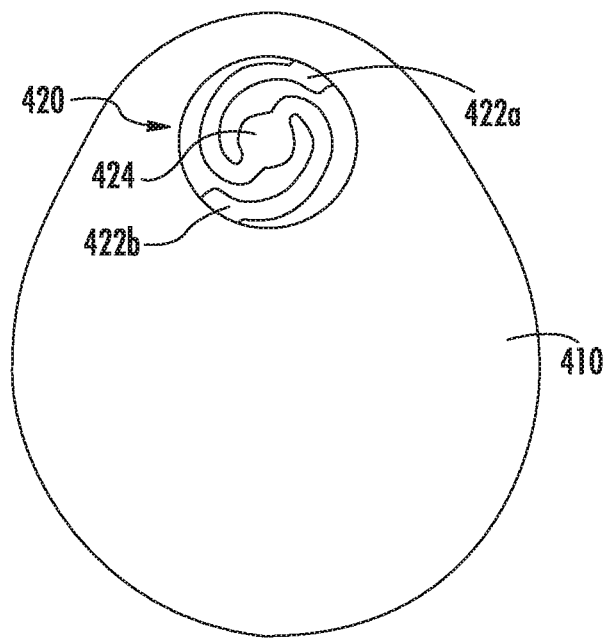
FIGS. 4A-4B show an example biosensor alignment and retention feature according to this disclosure.
Figure 4B:
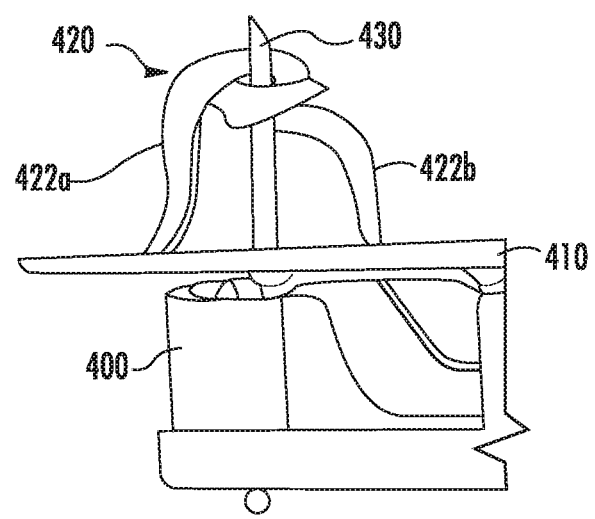

Referring now to FIGS. 4A-4B, FIGS. 4A-4B show an example sensor alignment and retention feature 420 (or just "retention feature") according to this disclosure. In this example, the retention feature 420 is coupled to a pad 410 that may be affixed to a lower surface of a biosensor, such as biosensor 400 shown in FIG. 4B. The retention feature 420 in this example has a central feature 424 that engages with and encircles the insertion needle 430 of a biosensor 400. In the example shown in FIG. 4A, the central feature 424 does not yet have an opening, such as a hole or slits (e.g., in an "|", "X", or "*" shape), cut in it to accommodate the insertion needle 430; however, the opening may be cut at any suitable point during the manufacturing process or it may be created when an insertion needle is inserted through the CGM and retention feature, which may occur during the manufacturing process or at the time the CGM is applied by the wearer.

Figure 5A:
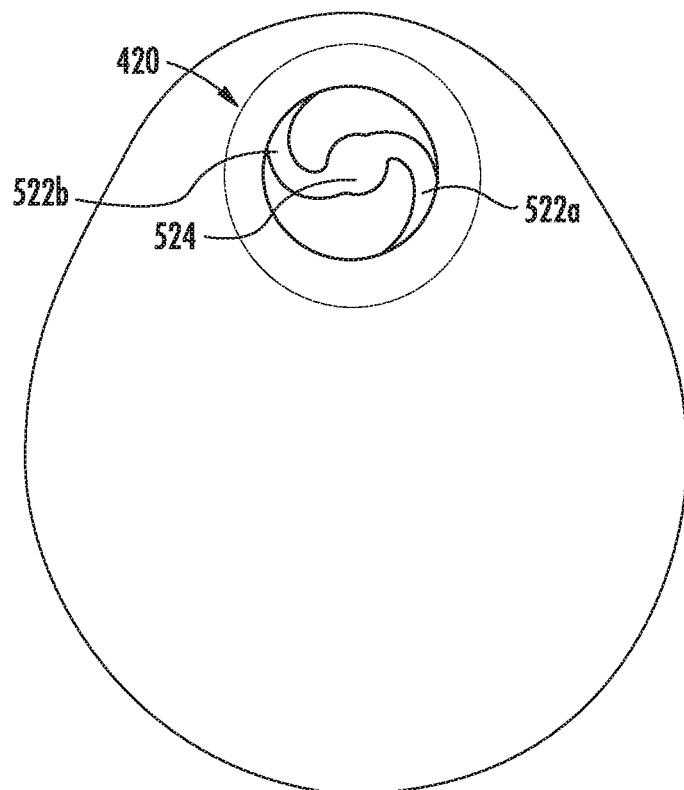
FIGS. 5A-5B show an example biosensor alignment and retention feature according to this disclosure.
Figure 5B:
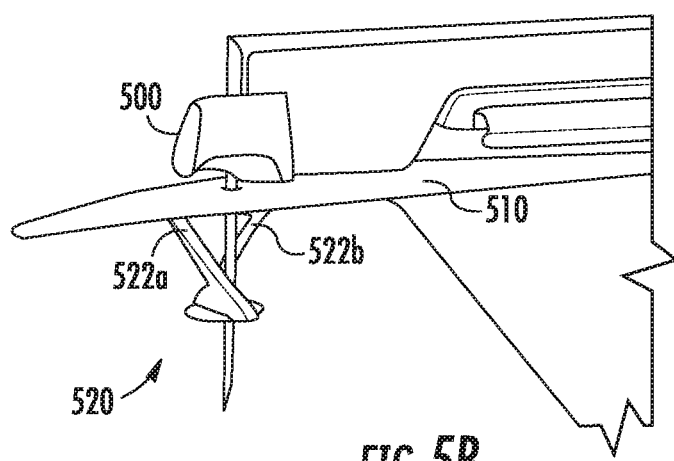

In addition to the central feature 424, the example retention feature 420 includes two legs 422a-b. Each leg 422a-b has two ends, one of which is coupled to a pad 410, or if no pad is used, to a ring or other feature that may be affixed to the bottom surface of a biosensor 400. The other end of each leg 422a-b is coupled to the central feature 424. In this example, the legs 422a-b attach at opposite sides of the central feature 424 and each then couple at a respective point on the pad 410 substantially 180 degrees around the central feature 424, i.e., 180 degrees offset from each other. In different examples, the legs may couple at different locations on the pad 410 relative to coupling points on the central feature 424, such as at 90 degrees offset, 120 degrees offset, etc. Further, while two legs 422a-b are shown in this example, in some examples, more than two legs may be employed. The two legs 422a-b allow the central feature 424 to extend away from the biosensor to engage with and encircle the insertion needle 430 at a location between the bottom surface of the biosensor 400 and the tip of the needle 430, as can be seen in FIG. 4B. In addition, the legs 422a-b allow the central feature 420 to collapse against the bottom surface of the biosensor 400 when it is applied to a wearer's skin Referring now to FIGS. 5A-5B, FIGS. 5A-5B show an example sensor alignment and retention feature 520 (or just "retention feature") according to this disclosure. In this example, the retention feature 520 is coupled to a pad 510 that may be affixed during manufacturing to a lower surface of a biosensor, such as biosensor 500 shown in FIG. 5B. Similar to the example shown in FIG. 4A, the retention feature 520 in this example has a central feature 524 that engages with and encircles the insertion needle 530 of a biosensor 500. In the example shown in FIG. 5A, the central feature 524 does not yet have an opening cut in it to accommodate the insertion needle 530; however, the opening may be cut at any suitable point during the manufacturing process. Alternatively, in some examples, the opening may be created when an insertion needle is inserted through the CGM and retention feature, which may occur during the manufacturing process or at the time the CGM is applied by the wearer.

In addition to the central feature 524, the example retention feature 520 includes two legs 522a-b. Similar to the example shown in FIG. 4A, each leg 522a-b has two ends, one of which is coupled to a pad 510, or if no pad is used, to a ring or other feature that may be affixed to the bottom surface of a biosensor 500. The other end of each leg 522a-b is coupled to the central feature 524. In this example, the legs 522a-b attach at opposite sides of the central feature 524 and each then couple at a respective point on the pad 510 substantially 90 degrees offset around the central feature 424. As discussed above with respect to FIGS. 4A and 4B, any suitable number of legs may be employed in different examples. For example, the retention feature 520 shown in FIG. 5A may be modified to add two additional legs, each of which may couple to the central feature 524 such that each of the legs couples at positions 90 degrees offset from each other, and the other ends of each leg likewise couple at positions 90 degrees offset from each other on the pad 510.

The two legs 522a-b in this example allow the central feature 524 to extend away from the biosensor 500 to engage with and encircle the insertion needle 530 at a location between the bottom surface of the biosensor 500 and the tip of the needle 530, as can be seen in FIG. 5B. In addition, the legs 522a-b allow the central feature 520 to collapse against the bottom surface of the biosensor 500 when it is applied to a wearer's skin. Thus, this example retention feature 520 provides alignment and retention of a sensor wire within a hollow insertion needle 530 used to apply an invasive biosensor 500.

Figure 6:
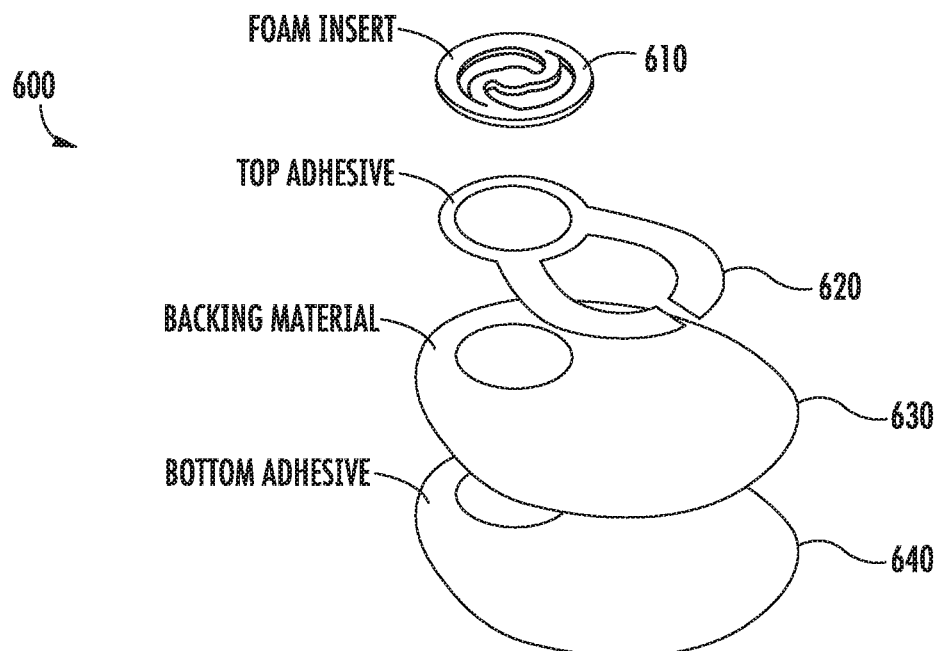
FIGS. 6-7 show example manufacturing techniques for alignment of biosensors and insertion needles according to this disclosure.

Referring now to FIG. 6, FIG. 6 shows an exploded view of an example pad and sensor alignment and retention assembly 600. The example alignment and retention assembly 600 includes four components that may be separately manufactured and assembled to provide sensor alignment and retention for an invasive biosensor. The assembly 600 includes a retention feature 610, a top-layer adhesive 620, a backing material 630, and a bottom-layer adhesive 640. In this example, the retention feature 610 has the same configuration as the retention feature 520 shown in FIGS. 5A-5B, which has two legs and a central feature. The retention feature 610 in this example is separately manufactured from a piece of polyurethane foam by cutting away portions of the foam to form the legs, central feature, and perimeter ring.

The top-layer adhesive 620 is a PSA that is applied to the backing material 630 during the manufacturing process. The PSA is applied to the perimeter of the retention feature 610 and is also applied to portions of the backing material 630 to provide adhesion between the backing material 630 and the bottom surface of a biosensor housing. In this example, the top-layer adhesive 620 is provided as a single piece of two-sided tape, but in some examples may be sprayed onto the backing material 630 or may include multiple pieces of tape. Further, the top-layer adhesive 620 may be applied at any suitable locations on the backing material 630 to provide adhesion between the backing material 630 and the retention feature 610, as well as between the backing material 630 and the bottom surface of a biosensor housing.

The backing material 630 in this example is constructed of a polyurethane-coated fabric; however, any suitable material may be employed, such as cloths, foams, etc. In this example, the backing material 630 has been cut from a sheet of material into a shape corresponding to the shape of a biosensor's housing and with a hole to correspond to the retention feature.

The bottom-layer adhesive 640 is a PSA that is applied to the backing material 630 and is intended to adhere the backing material 630, and thereby the invasive biosensor, to a wearer's skin. Thus, the bottom-layer adhesive 640 comprises an adhesive suitable for long-term contact with a person's skin. Such an adhesive may be water and humidity resistant. In this example, the adhesive comprises a two-sided tape that has been cut to a shape corresponding to the shape of the backing material 630. In some examples, the bottom-layer adhesive 640 may comprise another type of adhesive, such as a liquid that may be sprayed onto the backing material 630 or may include multiple pieces of tape.

To create the example assembly 600 shown in FIG. 6, the top-layer adhesive 620 is applied to one side of the backing material 630. The retention feature 610 is then pressed against a location on backing material 630 corresponding to the top-layer adhesive 620 and the hole formed in the backing material 630. The bottom-layer adhesive 640 is then applied to the other side of the backing material 630. It should be appreciated that the ordering of the steps described above may vary according to different manufacturing processes. In some examples, other steps may be included, steps described above may be omitted, or the steps may be performed in a different order. For example, the backing material 630, with the top-layer adhesive 620 and retention feature 610, may be adhered to a bottom surface of an invasive biosensor before the bottom-layer is applied. Still further variations are within the scope of the present disclosure.

Figure 7:
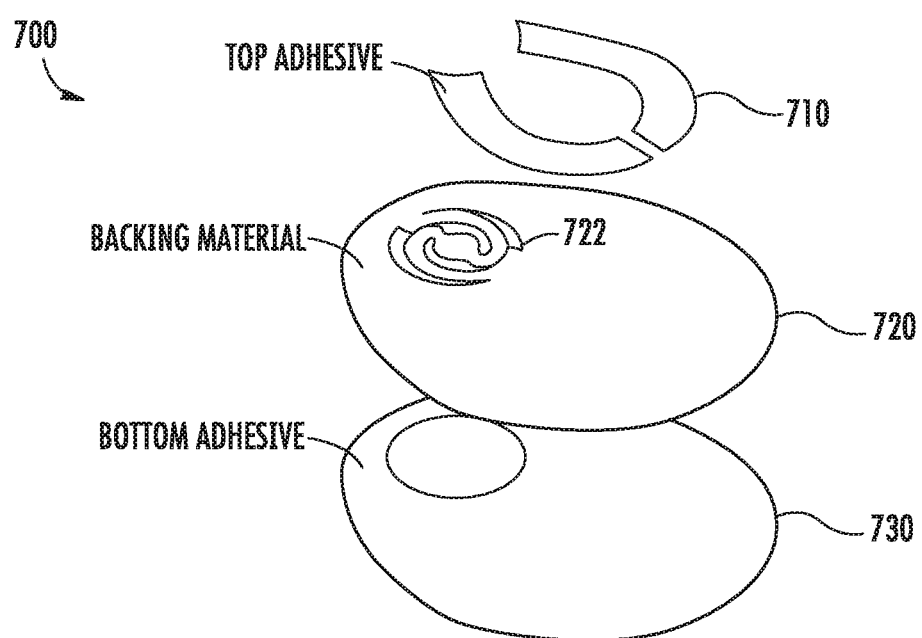

Referring now to FIG. 7, FIG. 7 shows an exploded view of an example pad and sensor alignment and retention assembly 700. In this example, the assembly includes a backing material 720 with a top-layer adhesive 710 and a bottom-layer adhesive 730.

Unlike the example assembly 600 shown in FIG. 6, in this example, the assembly has a retention feature 722 formed from the same piece of material as the backing material 720. Thus, rather than having two separate pieces, the backing material and the retention feature are formed from the same piece of material. A top-layer adhesive 710 may then be applied to one side of the backing material 720 to adhere the backing material to a bottom surface of an invasive biosensor. A bottom-layer adhesive 730 may be applied to the other side of the backing material 720 to adhere the backing material 720 to a wearer's skin. Suitable materials for the backing material 720 and retention feature 722 are described above, as are suitable adhesives for the top-layer and bottom-layer adhesives 710, 730.

Figure 8A:
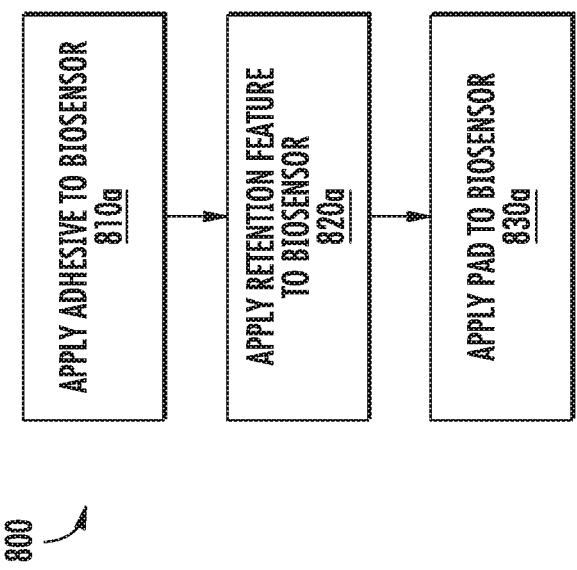
FIGS. 8A-8B show an example method for assembling a biosensor alignment and retention feature.
Figure 8B:
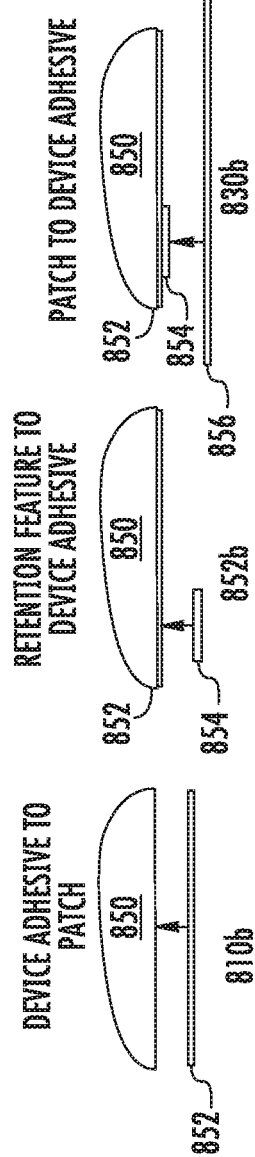

Referring now to FIGS. 8A-8B, FIGS. 8A-8B illustrate an example technique 800 for applying a retention feature to an invasive biosensor. In this example, an example backing material (or pad) and sensor alignment and retention assembly similar to the assembly 600 shown in FIG. 6 is employed, though any other suitable assembly according to this disclosure may be used. Specifically, the technique 800 described with respect to FIGS. 8A-8B relates to assemblies with distinct pads and retention features that are formed from different pieces of materials.

At block 810a of FIG. 8A, illustrated with corresponding diagram 810b, an adhesive 852 is applied to a biosensor housing 850. In this example, the top-layer adhesive 852 is a two-sided tape that is cut into a shape corresponding to the shape of the bottom surface of the housing 850 and is pressed against the bottom surface of the housing 850. In some examples, however, the adhesive 852 may be sprayed onto the housing, the housing 850 may be dipped into an adhesive, or any other suitable technique may be used to apply an adhesive to the bottom surface of the housing 850, such as heat staking to fuse the components together. In this example, the adhesive 852 is applied to the entire bottom surface of the housing; however, in some examples, the adhesive 852 may be applied at a location corresponding to a retention feature 854 and at one or more other locations corresponding to a pad 856 or multiple pads.

At block 820*a*, illustrated with corresponding diagram 820*b*, a retention feature 854 is affixed to the bottom surface of the housing 850 by pressing it against the adhesive 852. The retention feature 854 is applied at a location corresponding to where a sensor wire and needle extend (or will extend) from the bottom surface of the housing 850, such that an opening on the retention feature 934 are aligned with the exit point of the sensor wire from the bottom surface of the housing 850.

At block 830*a*, illustrated with corresponding diagram 830*b*, a pad 856 is affixed to the bottom surface of the housing 850 by pressing it against the adhesive 852. In this example, the retention feature 854 is not separately adhered to the pad 856, but instead, the pad 856 has a cut-out corresponding to the retention feature so that the pad 856 may adhere to the housing 850 while not interfering with the retention feature's function.

After the pad 856 has been affixed to the bottom surface of the housing 850, an adhesive may be applied to the exposed surface of the pad 856 to allow the pad 856 to be affixed to a wearer's skin Such additional adhesive may be applied before the pad 856 is affixed to the housing 850 or afterwards. Further, such additional adhesive may be applied as a tape or may be sprayed onto the pad 856.

It should be appreciated that the ordering of the steps described above with respect to the method 800 of FIG. 8A may vary according to different manufacturing processes. In some examples, other steps may be included, steps described above may be omitted, or the steps may be performed in a different order. For example, the adhesive 852 may be separately applied to the retention feature 854 and the pad 856, which may be pressed against the bottom surface of the housing 850. Still further variations are within the scope of the present disclosure.

Referring now to FIGS. 9A-9B, FIGS. 9A-9B illustrate an example technique 900 for applying a retention feature to an invasive biosensor. In this example, an example pad and sensor alignment and retention assembly similar to the assembly 600 shown in FIG. 6 is employed, though any other suitable assembly according to this disclosure may be used. Specifically, the technique 900 described with respect to FIGS. 9A-9B relates to assemblies with distinct pads and retention features that are formed from different pieces of materials.

At block 910*a*, illustrated with corresponding diagram 910*b*, a retention feature 934 is affixed to the bottom surface of the housing 930 by applying an adhesive to a portion of the retention feature 932 and pressing the retention feature 934 against the housing. For example, referring again to the retention feature 600 shown in FIG. 6, an adhesive 932 may be applied to one side of the ring encircling the legs and center feature of the retention feature. Thus, the retention feature 934 may be applied to the housing while allowing the legs and center feature to extend away from the housing 930 and engage with an insertion needle. After the adhesive 932 has been applied to the retention feature 934, it may be affixed to the housing 930 by pressing it against the housing 930. The retention feature 934 is applied to the housing 930 at a location corresponding to where a sensor wire and needle extend (or will extend) from the bottom surface of the housing 930, and such that a hole or slit(s) on the retention feature 934 are aligned with the exit point of the sensor wire from the bottom surface of the housing 930.

At block 920*a*, illustrated with corresponding diagram 920*b*, a pad 938 is affixed to the bottom surface of the housing 930 by applying an adhesive 936 to one side of the pad 938, and pressing it against the bottom surface of the housing 930. In this example, the pad 938 has a cut-out corresponding to the retention feature 934 so that the pad may adhere to the housing 930 while not interfering with the retention feature's function.

After the pad 938 has been affixed to the bottom surface of the housing 930, an adhesive may be applied to the exposed surface of the pad 938 to allow the pad 938 to be affixed to a wearer's skin. Such additional adhesive may be applied before the pad 938 is affixed to the housing 930 or afterwards. Further, such additional adhesive may be applied as a tape or may be sprayed onto the pad 938.

It should be appreciated that the ordering of the steps described above with respect to the method 900 of FIG. 9A may vary according to different manufacturing processes. In some examples, other steps may be included, steps described above may be omitted, or the steps may be performed in a different order. For example, the adhesive 932 may be applied to the housing 930, and the retention feature 944 may then adhered to the housing 930. Similarly, the adhesive 936 may be applied to the housing 930, and the pad 938 may then be pressed against the bottom surface of the housing 850. Still further variations are within the scope of the present disclosure.

Figure 10A:
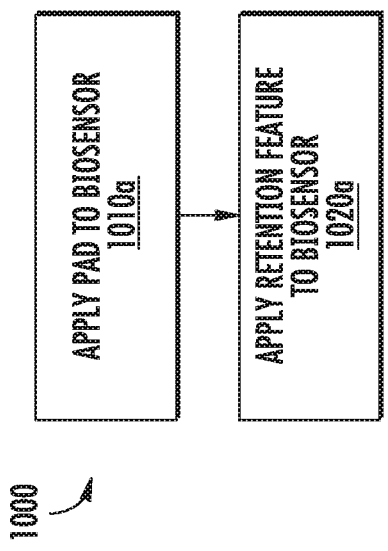
FIGS. 10A-10B show an example method for assembling a biosensor alignment and retention feature.
Figure 10B:
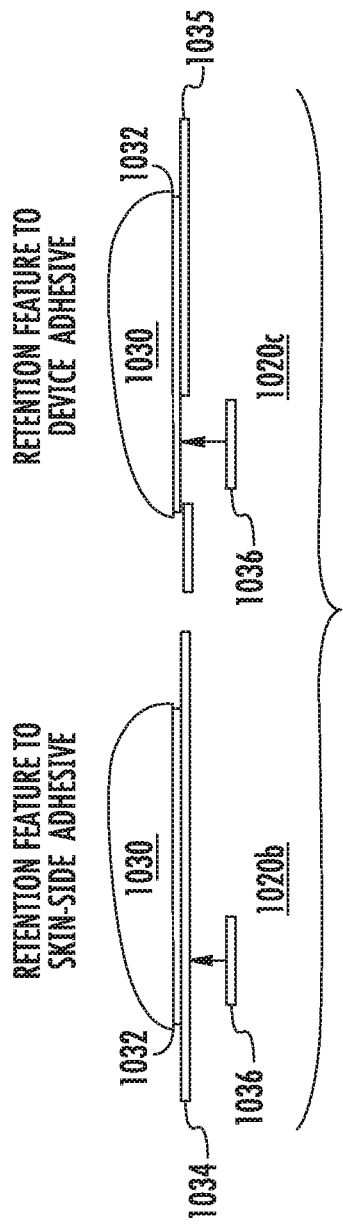

Referring now to FIGS. 10A-10B, FIGS. 10A-10B illustrate an example technique 1000 for applying a retention feature to an invasive biosensor. In this example, an example pad and sensor alignment and retention assembly similar to the assembly 600 shown in FIG. 6 is employed, though any other suitable assembly according to this disclosure may be used. Specifically, the technique 1000 described with respect to FIGS. 10A-10B relates to assemblies with distinct pads and retention features that are formed from different pieces of materials.

At block 1010*a*, a pad 1034 is affixed to the bottom surface of the housing 930. The adhesive 1032 may be applied to the housing 1030 or it may be applied to the pad 1034. The pad 1034 is then affixed to the housing 1030 by pressing it against the bottom surface of the housing 1030.

At block 1020*a*, illustrated with corresponding diagrams 1020*b* and 1020*c*, a retention feature is applied to the biosensor. With respect to example 1020*b*, the pad 1034 is shaped to correspond to a shape of the housing 1030, though it has portions that extend beyond the edges of the housing 1030. In addition, while the pad 1034 has an opening cut in it to accommodate a sensor wire and insertion needle, the retention feature is affixed to the pad 1034, rather than the housing 1030. In this example, an adhesive is applied to the bottom surface of the pad, such as an adhesive suitable for adhering the pad 1034 to a wearer's skin. The retention feature 1036 is then pressed against the pad and is affixed by the adhesive.

With respect to example 1020*c*, a pad 1035 is shaped to correspond to a shape of the housing 1030, though it has portions that extend beyond the edges of the housing 1030. In addition, the pad 1035 has a portion cut out of it to allow the retention feature 1036 to be affixed directly to the housing 1030 by the adhesive 1032. The retention feature 1036 is inserted into the cut-out in the pad 1034, pressed against the housing 1030 and is affixed by the adhesive 1032.

The retention feature 1036 is applied to the housing 1030 at a location corresponding to where a sensor wire and needle extend (or will extend) from the bottom surface of the housing 1030, and such that an opening on the retention feature 1036 are aligned with the exit point of the sensor wire from the bottom surface of the housing 1030. Further, after the pad 1034 has been affixed to the bottom surface of the housing 1030, an adhesive may be applied to the exposed surface of the pad 1034 to allow the pad 1034 to be affixed to a wearer's skin. Such additional adhesive may be applied before the pad 1034 is affixed to the housing 1030 or afterwards. Further, such additional adhesive may be applied as a tape or may be sprayed onto the pad 1034.

Figure 11A:
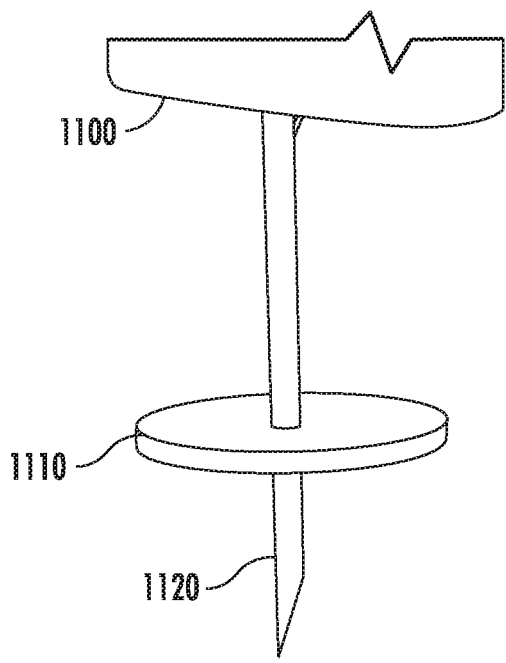
FIGS. 11A-11B show an example biosensor alignment and retention feature.
Figure 11B:
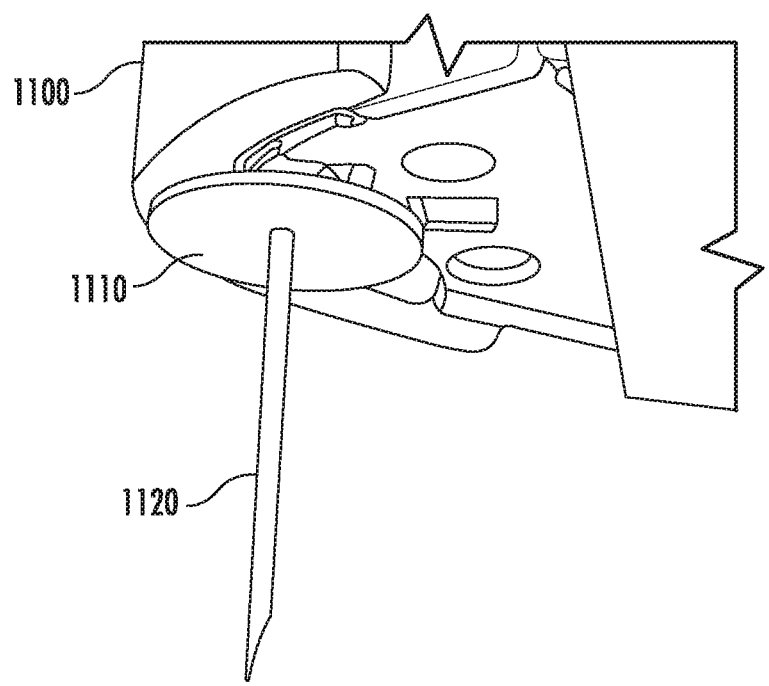

Referring now to FIGS. 11*a*-11*b*, FIGS. 11*a*-*b* illustrate an example sensor alignment and retention feature 1110. In this example, the retention feature 1110 is a disk of material with an opening cut into it to allow an insertion needle and sensor wire to be inserted through the retention feature 1110. The retention feature 1110 in this example, unlike the previous examples, is not affixed to the housing or a pad, but instead is positioned along the length of the insertion needle 1120 between the bottom of the invasive sensor 1100 and the tip of the needle 1120 and held in place through the tight fit of the needle through the material. Thus, the retention feature 1110 engages with and encircles the needle 1120, thereby maintaining the sensor wire within the hollow portion of the sensor wire. While in this example, the retention feature 1110 has a circular shape, however, any suitable shape for the retention feature may be employed.

FIG. 11*a* illustrates the retention feature 1110 installed on the insertion needle before the biosensor is affixed to a wearer. FIG. 11*b* illustrates how the retention feature 1110 collapses against the bottom surface of the biosensor 1100 after the biosensor has been affixed to a wearer. This example retention feature 1110 slides upwards along the needle 1120 until it is pressed against the underside of the biosensor.

Figure 12A:
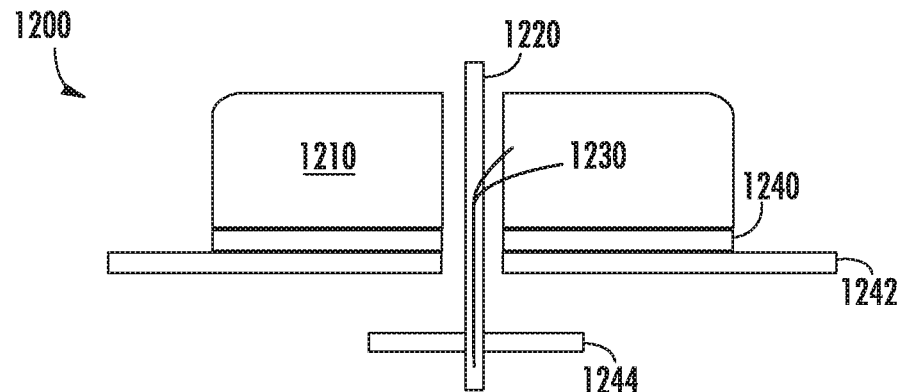
FIGS. 12A-12B show an example biosensor alignment and retention feature.
Figure 12B:
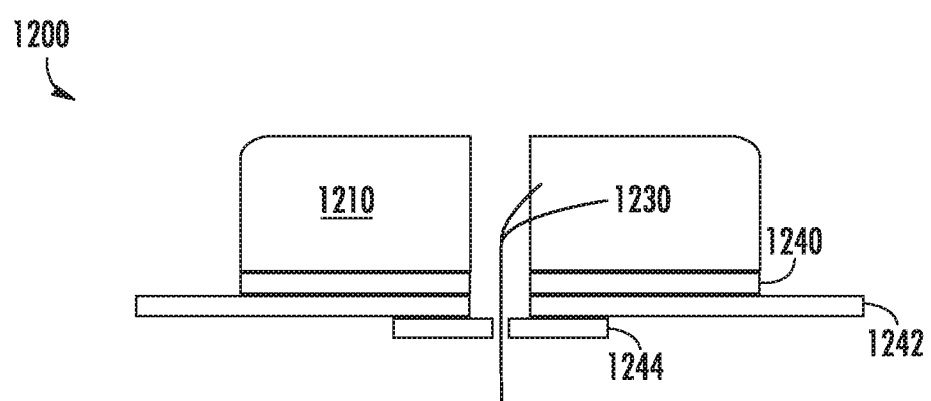

Referring now to FIGS. 12*a*-12*b*, FIGS. 12*a*-*b* illustrate an example sensor alignment and retention feature 1244. Shown in FIG. 12*a* is a biosensor 1200 having a housing 1210 to which a pad 1242 is adhered by an adhesive 1240. A sensor wire 1230 extends through a cavity defined in the housing 1210 and down through a hole in the bottom surface of the housing 1210. In addition, an insertion needle 1220 has been inserted through a hole defined in the upper surface of the housing 1210, through a cavity defined between the holes in the upper surface and lower surface of the housing 1210, and out through the bottom of the biosensor 1200. As is shown, a portion of the sensor 1230 is positioned within a hollow portion of the insertion needle 1220 such that the two are co-axially aligned.

In this example, a retention feature 1244 is shown that is similar to the retention feature 1110 shown in FIGS. 11A-11B. Specifically, the retention feature 1244 is engaged with an insertion needle 1220, but is not otherwise affixed to the biosensor 1200. Instead, the retention feature 1244, prior to the biosensor 1200 being affixed to a wearer, is positioned on the needle between the pad 1242 and the tip of the needle 1220.

FIG. 12*b* illustrates the biosensor 1200 after it has been applied to a wearer and the insertion 1220 needle has been withdrawn. The retention feature 1244 has been forced upward into contact with the pad 1242, and the sensor wire 1230 has been left in place within the wearer's skin. The retention 1244 feature can adhere to the bottom of the pad 1242 as the underside of 1242 is coated with adhesive to attach to the skin. Thus, at a later time when the biosensor 1200 is removed, the retention feature 1244 will be removed with the biosensor 1200.

Figure 13A:
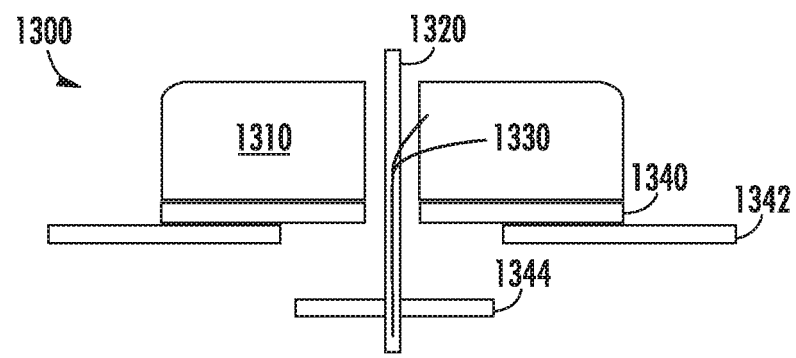
FIGS. 13A-13B show an example biosensor alignment and retention feature.
Figure 13B:
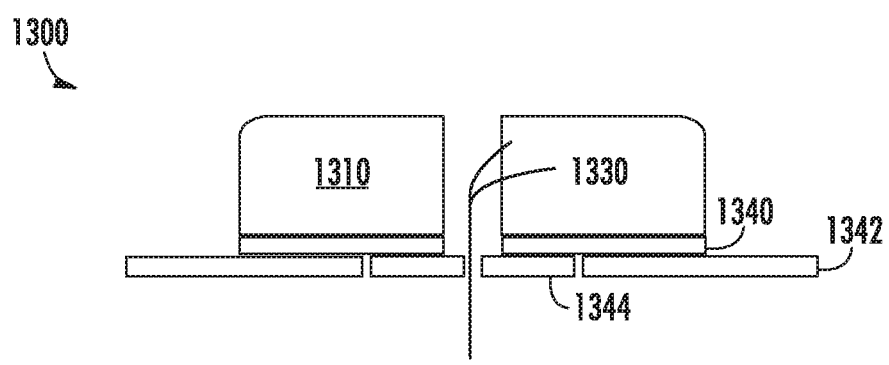

Referring now to FIGS. 13*a*-13*b*, FIGS. 13*a*-*b* illustrate an example sensor alignment and retention feature 1344. Shown in FIG. 13*a* is a biosensor 1300 having a housing 1310 to which a pad 1342 is adhered by an adhesive 1340. A sensor wire 1330 extends through a cavity defined in the housing and down through a hole in the bottom surface of the housing 1330. In addition, an insertion needle 1320 has been inserted through a hole defined in the upper surface of the housing 1310, through a cavity defined between the holes in the upper surface and lower surface of the housing 1310, and out through the bottom of the biosensor 1300. As is shown, a portion of the sensor 1330 is positioned within a hollow portion of the insertion needle 1320 such that the two are co-axially aligned.

This example is similar to the example shown in FIGS. 12A-12B, however, as can be seen, the pad 1342 in FIGS. 13A-13B has a portion cut out to allow the retention feature to slide up against the housing and lie flush with the pad 1342. Thus, after the biosensor 1300 has been affixed to a wearer's skin and the insertion needle 1320 has been removed, the retention feature 1344 has slide upwards into the cut out area within the pad 1342, allowing it to lie flush with the pad 1342, and to adhere it to the housing 1310 through the adhesive 1340. Thus, at a later time when the biosensor 1300 is removed, the retention feature 1344 will be removed with the biosensor 1300.

Referring now to FIGS. 14A-14C, FIGS. 14A-14C show an example sensor alignment and retention feature 1430 according to this disclosure. In this example, an invasive biosensor 1400 includes a sensor wire 1410 that extends out from a bottom surface of the biosensor 1400. An insertion needle 1420 has been inserted through the biosensor and aligned co-axially with the sensor wire 1410. The retention feature 1430 in this example has a shape similar to a stopper having an opening formed through it to accommodate the insertion needle 1430, and is composed of an elastomeric material such as silicone rubber or other.

The retention feature 1430 has a flat bottom surface 1432 that will become flush with the bottom surface of the biosensor 1400 once the biosensor 1400 has been affixed to a wearer's skin. As can be seen, and similar to the disk 1344 shown in FIGS. 13A-13B, the retention feature 1410 is attached to a portion of the insertion needle through an interference fit, but is not otherwise attached to the biosensor 1400 as shown in FIGS. 14A-14B. When the biosensor 1400 is applied to a wearer's skin, the retention feature 1430 slides upwards along the needle 1420 and into a cavity 1402 defined in the underside of the biosensor 1400, thereby allowing the retention feature 1430 to collapse into and be retained by the biosensor 1400, as can be seen in FIG. 14C.

Figure 15:
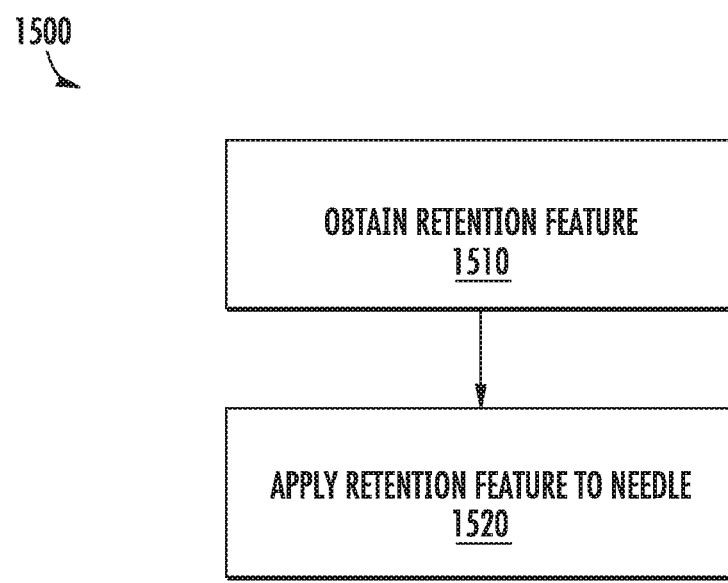
FIG. 15 shows an example method for assembling a biosensor alignment and retention feature.

Referring now to FIG. 15, FIG. 15 shows an example method 1500 for invasive biosensor alignment and retention according to this disclosure. The method 1500 will be described with respect to the example retention feature 1430 shown in FIGS. 14A-14B; however, any suitable retention feature or means for according to this disclosure may be employed according to different examples.

At block 1510, a biosensor is obtained. In this example, the biosensor is obtain by constructing a biosensor. The biosensor is constructed by obtaining a housing having a first surface defining a first opening, and a second surface opposite the first surface defining a second opening, the first and second openings defining a substantially unobstructed pathway through the housing.

After obtaining the housing, a biosensor wire is positioned within the housing and oriented so that a first portion of the biosensor wire extends through the first opening and out of the housing. A hollow insertion needle is then inserted into and through the unobstructed pathway from the second opening and through the first opening such that the hollow insertion needle at least partially encircles the portion of the biosensor wire that extends out of the housing.

At block 1520, a retention feature 1430 is obtained. For example, the retention feature 1430 may be received during a manufacturing process, such as by an automated machine operating as a part of an assembly line. In one example, the retention feature 1430 is picked by a robotic arm. In some examples, a retention feature cd1430 may be provided in an uncut sheet of material having one or more preformed retention features 1430.

At block 1520, the retention feature 1430 is attached to the needle 1420 of a biosensor 1400. In this example, and as described above, the needle 1420 is inserted through the housing of a biosensor 1430, such as through a hole in the upper surface of the biosensor 1400, through a cavity formed within the biosensor 1420, and out through a hole in the lower surface of the biosensor 1400. Further, the needle 1420 is co-axially aligned with a sensor wire 1410 that is mounted within the biosensor, but extends downward through a hole in the bottom surface of the biosensor 1400 and is positioned within a hollow portion of the needle 1420.

In this example, an opening formed in the retention feature 1430 is aligned with the needle 1420, and the retention feature 1430 is pressed onto the needle 1420 and slid along a portion of the length of the needle 1420. The distance the retention feature 1430 is slid along the length of the needle 1420 may vary according to different examples, however, in this example, the retention feature 1430 is ultimately positioned to allow approximately 1-5 mm of the needle 1420, including the sharp tip of the needle 1420, to protrude from the retention feature 1430. In some examples, the retention feature 1430 may be positioned such that no portion of the needle 1420 protrudes from the retention feature 1430, but the sharp tip of the needle 1420 is substantially aligned with the flat bottom surface 1432 of the retention feature 1430. Such positioning may provide sensor alignment and retention functionality and may also shield the end of the needle 1420 to prevent it unintentionally contacting the wearer or some other object prior to being inserted into the wearer's skin.

In this example, the needle 1420 is pressed through a hole formed in the retention feature 1430; however, in some examples, a retention feature may be formed without such a hole. Thus, the needle may be pressed through the retention feature to form a hole and to couple the retention feature to the needle.

In some examples, at block 1520 a retention feature 1430 may be applied, as well as other components, such as one or more adhesives or a pad, such as described above with respect to FIGS. 8A-8B, 9A-9B, or 10A-10B.

In some examples, such as with respect to the examples shown in FIGS. 11A-11B, 12A-12B, or 13A-13B, the retention feature 1430 discussed above may be replaced with a disk, such as the disk 1110 shown in FIGS. 11A-11B. In addition, one or more pads or adhesives may be applied, such as shown in FIGS. 12A-12B and 13A-13B, as discussed above with respect to the methods 800-1000 of FIGS. 8A-8B, 9A-9B, or 10A-10B.

Figure 16:
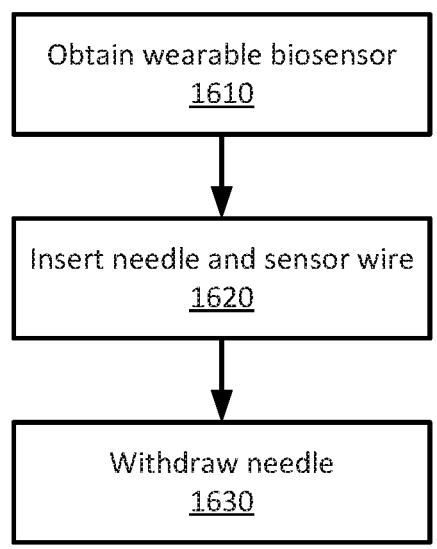
FIG. 16 shows an example method for applying a wearable biosensor having a biosensor alignment and retention feature.

Referring now to FIG. 16, FIG. 16 shows a method 1600 for applying a wearable biosensor having a biosensor retention feature. The example method of FIG. 16 will be described with respect to the example biosensor 1100 shown in FIGS. 11A-11B; however, any suitable wearable biosensor and biosensor retention feature according to this disclosure may be employed.

At block 1610, a wearer obtains a wearable biosensor 1100 having a biosensor retention feature 1110 encircling and contacting a hollow insertion needle inserted through the housing of the biosensor and co-axially aligned with a portion of a sensor wire extending from the housing of the biosensor.

At block 1620, the wearer applies the wearable biosensor 1100 by inserting the hollow insertion needle 1120 into the wearer's skin through a puncture at the desired location on the wearer's skin. The wearer inserts the biosensor wire through the puncture as well, taking advantage of the coaxial alignment between the biosensor wire and the hollow insertion needle 1120, by pressing the wearable biosensor's housing against the wearer's skin, thereby collapsing the biosensor retention feature against the housing.

At block 1630, the wearer withdraws the insertion needle from the puncture and the housing, leaving the wearable biosensor affixed to the wearer's skin and the biosensor wire inserted through the patient's skin.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A wearable biosensor device comprising:
   a housing comprising:
      a first surface defining a first opening, the first surface configured to be coupled to a skin of a wearer, and
      a second surface opposite the first surface, the second surface defining a second opening, the first and second openings defining a substantially unobstructed pathway through the housing;
   a biosensor wire partially disposed within the housing and having an exterior portion extending through the first opening;
   a hollow insertion needle positioned within the pathway and extending through the first opening, the hollow insertion needle at least partially encircling the biosensor wire; and a biosensor retention feature collapsible against the first surface of the housing, the biosensor retention feature encircling and contacting the hollow insertion needle.

2. The wearable biosensor device of claim 1, wherein the biosensor retention feature comprises a patch, an inner ring member, an outer ring member, and at least one flexible leg member coupling the inner ring member to the outer ring member, the inner ring member encircling and contacting the hollow insertion needle, the outer ring member affixed to the patch, and the patch affixed to the first surface of the housing.

3. The wearable biosensor device of claim 2, wherein the biosensor retention feature comprises a plurality of flexible leg members coupling the inner ring member to the outer ring member, each of the flexible leg members attaching to the inner ring member at a respective first contact point and the outer ring member at a respective second contact point.

4. The wearable biosensor device of claim 3, wherein the respective first and second contact points for at least one flexible leg member are offset from each other.

5. The wearable biosensor device of claim 1, wherein the biosensor retention feature comprises a disk defining a hole, the insertion needle and biosensor wire extending through the hole in the disk, the disk spaced apart from the first surface of the housing.

6. The wearable biosensor device of claim 5, wherein the biosensor retention feature comprises a flexible material.

7. The wearable biosensor device of claim 4, wherein the flexible material comprises a polyurethane foam material or a silicone material.

8. The wearable biosensor device of claim 5, wherein the biosensor retention feature is adapted to enable the disk to slide along the hollow insertion needle and into contact with the first surface of the housing in response to a force applied to a bottom surface of the disk.

9. The wearable biosensor device of claim 1, wherein the biosensor retention feature comprises a stopper-shaped member defining a hole extending through the stopper-shaped member, the insertion needle and biosensor wire extending through the hole in the stopper-shaped member.

10. The wearable biosensor device of claim 9, wherein the stopper-shaped member is configured to slide along the hollow insertion needle and into an opening defined in the first surface of the housing in response to a force applied to a bottom surface of the stopper-shaped member.

11. The wearable biosensor device of claim 1, further comprising a pad affixed to the first surface of the housing, the retention feature coupled to the pad and extending away from the pad.

12. The wearable biosensor device of claim 1, further comprising a pad affixed to the first surface of the housing, the retention feature not coupled to the pad, the pad defining a cutout portion corresponding to the retention feature, the retention feature configured to collapse against the housing and into the cutout portion defined by the pad.

13. A wearable biosensor device comprising:
a housing comprising:
a first surface defining a first opening, the first surface configured to be coupled to a skin of a wearer, and
a second surface opposite the first surface, the second surface defining a second opening, the first and second openings defining a substantially unobstructed pathway through the housing;
a biosensor wire partially disposed within the housing and having an exterior portion extending through the first opening;
a hollow insertion needle positioned within the pathway and extending through the first opening coaxially aligned with the exterior portion of the biosensor, the hollow insertion needle at least partially encircling the exterior portion of the biosensor wire; and
means for maintaining coaxial alignment between the hollow insertion needle and the biosensor wire coupled to a portion of the hollow insertion needle coaxially aligned with the exterior portion of the biosensor wire.

14. The wearable biosensor device of claim 13, wherein the means for maintaining coaxial alignment includes at least one flexible leg.

15. The wearable biosensor device of claim 13, wherein the means for maintaining coaxial alignment is spaced apart from the housing.

* * * * *